US006685810B2

(12) United States Patent
Noca et al.

(10) Patent No.: US 6,685,810 B2
(45) Date of Patent: Feb. 3, 2004

(54) DEVELOPMENT OF A GEL-FREE MOLECULAR SIEVE BASED ON SELF-ASSEMBLED NANO-ARRAYS

(75) Inventors: Flavio Noca, Altadena, CA (US); Jingming Xu, Providence, RI (US); Daniel S. Choi, Los Angeles, CA (US); Brian D. Hunt, La Crescenta, CA (US); Michael E. Hoenk, Valencia, CA (US); Robert S. Kowalczyk, Santa Clarita, CA (US)

(73) Assignees: California Institute of Technology, Pasadena, CA (US); Brown University Research Foundation, Providence, RI (US)

( * ) Notice: Subject to any disclaimer, the term of this patent is extended or adjusted under 35 U.S.C. 154(b) by 106 days.

(21) Appl. No.: 09/791,493

(22) Filed: Feb. 22, 2001

(65) Prior Publication Data
US 2003/0052006 A1 Mar. 20, 2003

Related U.S. Application Data
(60) Provisional application No. 60/184,201, filed on Feb. 22, 2000.

(51) Int. Cl.[7] ............... G01N 27/447; G01N 27/453
(52) U.S. Cl. ................ 204/450; 204/600; 210/500.22
(58) Field of Search ................ 204/450, 451, 204/600, 601; 422/50, 70, 99; 435/287.2, 321.84, 490; 210/500.22, 500.26; 216/2, 56

(56) References Cited

U.S. PATENT DOCUMENTS

| | | | |
|---|---|---|---|
| 5,110,339 A | | 5/1992 | Ciriello et al. |
| 5,246,866 A | * | 9/1993 | Nasu et al. ............... 204/461 |
| 5,837,115 A | | 11/1998 | Austin et al. |
| 6,027,623 A | * | 2/2000 | Ohkawa ................... 204/450 |
| 6,033,546 A | * | 3/2000 | Ramsey .................... 204/603 |
| 6,120,667 A | * | 9/2000 | Hayashizaki et al. ....... 204/603 |
| 6,156,273 A | * | 12/2000 | Regnier et al. ............ 422/70 |
| 6,254,754 B1 | * | 7/2001 | Ross et al. ................ 204/548 |
| 6,368,871 B1 | * | 4/2002 | Christel et al. ........... 436/180 |

FOREIGN PATENT DOCUMENTS

EP 0679881 A1 * 11/1995

OTHER PUBLICATIONS

Avrutsky et al. ("Multiwavelength Diffraction and Apodization using Binary Superimposed Gratings," IEEE Photonics Technology Letters, vol. 10, No. 6, Jun. 1998).*
CAPLUS abstract of Spang–Thomsen et al. ("Estimation by flow cytometric DNA analysis of the effect of radiotherapy, hormone therapy and chemotherapy on human tumors grown in nude mice," Immune–Defic. Anim., Int. Workshop Immune–Defic. Anim. Exp. Res., 4th (1984), Meeting Date 1982, 409–415. Eds. Sordal, Bernard.*
Avrutsky, Ivan A. et al.; *Multiwavelength Diffraction and Apodization Using Binary Superimposed Gratings*; IEEE Photonics Technology Letters; vol. 10, No. 6, Jun. 1998; pp. 839–841.

(List continued on next page.)

*Primary Examiner*—T. Tung
*Assistant Examiner*—Alex Noguerola
(74) *Attorney, Agent, or Firm*—Christie, Parker & Hale, LLP (57) ABSTRACT

A device for utilizing a non-gel self-assembled nano-feature array molecular sieve for analyzing molecules is provided. The molecular sieve device comprises an ordered array of self-assembled nano-features which function as a molecular sieve to separate molecules based on a suitable characteristic. A system for integrating the non-gel ordered self-assembled nano-feature array molecular sieve of this invention into a device for separating molecules based on a characteristic and a method for separating a wide range of molecules using the non-gel ordered self-assembled nano-feature array molecular sieve of the invention are also provided.

40 Claims, 6 Drawing Sheets

OTHER PUBLICATIONS

Baughman, Ray H. et al.; *Carbon Nanotube Actuators*; Science; vol. 284; May 21, 1999; pp. 1340–1344.

Boul, P.J. et al.; *Reversible sidewall functionalization of buckytubes*; Chemical Physics Letters; vol. 310; Sep. 3, 1999; pp. 367–372.

Chen, Yan et al.; *Plasma–induced low temperature growth of graphitic nanofibers on nickel substrates*; Journal of Crystal Growth; vol. 193; Jun. 5, 1998; pp. 342–346.

Choi, Young Chul et al.; *Growth of carbon nanotubes by microwave plasma–enhanced chemical vapor deposition at low temperature*; J. Vac. Sci. Technol., American Vacuum Society; vol. 18, No. 4; Jul./Aug. 2000; pp. 1864–1868.

Chou, Hou–Pu et al.; *A microfabricated device for sizing and sorting DNA molecules*; Proc. Natl. Acad. Sci. USA, Applied Physical Sciences, Biophysics; vol. 96; Jan. 1999; pp. 11–13.

Dial, O. et al; *Fabrication of high–density nanostructures by electron beam lithography*; J. Vac. Sci. Technol.; vol. 16, No. 6; Nov./Dec. 1998; pp. 3887–3890.

Drmanac, R. et al.; *Sequencing by Hybridization*; Adams M.D. et al. "Automated DNA sequencing and analysis" Academic Press; pp. 29–36.

Duke, Thomas A. et al.; *Pulsed–field electrophoresis in microlithographic arrays*; Electrophoresis; vol. 17, 1996; pp. 1075–1079.

Fan, Shoushan et al.; *Self–Oriented Regular Arrays of Carbon Nanotubes and Their Field Emission Properties*; Science; vol. 283; Jan. 22, 1999; pp. 512–514.

Hadd, Andrew G. et al.; *Sub–microliter DNA sequencing for capillary array electrophoresis*; Journal of Chromatography A; vol. 894; 2000; pp. 191–201.

Hafner, Jason H. et al.; *Direct Growth of Single–Walled Carbon Nanotube Scanning Probe Microscopy Tips*; J. Am. Chem. Soc., The American Chemical Society; vol. 121; 1999; pp. 9750–9751.

Han, J. et al.; *Entropic Trapping and Escape of Long DNA Molecules at Submicron Size Constriction*; Physical Review Letters, The American Physical Society; vol. 83, No. 8; Aug. 23, 1999; pp. 1688–1691.

Han, Jie et al; *Observation and modeling of single–wall carbon nanotube bend junctions*; Physical Review B, The American Physical Society; vol. 57, No. 23; Jun. 15, 1998; pp. 983–989.

Han, Young–Soo et al.; *Synthesis of carbon nanotube bridges on patterned silicon wafers by selective lateral growth*; Journal of Applied Physics, American Institute of Physics; vol. 90, No. 11; Dec. 1, 2001; pp. 5731–5734.

Huang, Z.P. et al.; *Growth of highly oriented carbon nanotubes by plasma–enhanced hot filament chemical vapor deposition*; Applied Physics Letters, American Institute of Physics; vol. 73, No. 26; Dec. 28, 1998; pp. 3845–3847.

Hutt, Lester D. et al.; *Microfabricated Capillary Electrophoresis Amino Acid Chirality Analyzer for Extraterrestrial Exploration*; Analytical Chemistry; vol. 71, No. 18; Sep. 15, 1999; pp. 4000–4006.

Ilic, B. et al.; *Mechanical resonant immunospecific biological detector*; Applied Physics Letters, American Institute of Physics; vol. 77, No. 3; Jul. 17, 2000; pp. 450–452.

Ju, Jingyue et al.; *Energy transfer primers: A new fluorescence labeling paradigm for DNA sequencing and analysis*; Nature Medicine; vol. 2, No. 2; Feb. 1996; pp. 246–249.

Kelly, Ross T.; *Unidirectional rotary motion in a molecular system*; Nature; vol. 401; Sep. 9, 1999; pp. 150–152.

Kim, Philip et al.; *Nanotube Nanotweezers*; Science; vol. 286; Dec. 10, 1999; pp. 2148–2150.

Koumura, Nagatoshi et al.; *Light–driven monodirectional molecular rotor*; Nature, vol. 401; Sep. 9, 1999; pp. 152–155.

Lee, Cheol Lin et al.; *Low–temperature growth of carbon nanotubes by thermal chemical vapor deposition using Pd, Cr, and Pt as co–catalyst*; Chemical Physics Letters; vol. 327; Sep. 15, 2000; pp. 277–283.

Li, Y.J. et al.; *Carbon nanotube films prepared by thermal chemical vapor deposition at low temperature for field emission applications*; Applied Physics Letters, American Institute of Physics; vol. 79, No. 11; Sep. 10, 2001; pp. 1670–1672.

Liu, Q. et al.; *Detection of Virtually All Mutations–SSCP–(DOVAM–S): A Rapid Method for Mutation Scanning with Virtually 100*
Sensity; BioTechniques; vol. 26, No. 5; May 1999; pp. 932–942.

Masuda, Hideki et al.; *Highly ordered nanochannel–array architecture in anodic alumina*; Appl. Phys. Lett., American Institute of Physics; vol. 71, No. 19; Nov. 10, 1997; pp. 2770–2772.

Merkulov, V.I. et al.; *Patterned growth of individual and multiple vertically aligned carbon nanofibers*; Applied Physics Letters, American Institute of Physics; vol. 76, No. 24; Jun. 12, 2000, pp. 3555–3557.

Murakami, Hirohiko et al.; *Field emission from well–aligned, patterned, carbon nanotube emitters*; Applied Physics Letters, American Institute of Physics; vol. 76, No. 13; Mar. 27, 2000; pp. 1776–1778.

Nakamura, S.; *InGaN–based violet laser diodes*; Semicond Sci. Technol.; vol. 14; 1999; pp. R27–R40.

Öttinger, Hans Christian; *A thermodynamically admissible reptation model for fast flows of entangled polymers*; The Society of Rheology, Inc.; J. Rheol; vol. 43, No. 6; Nov./Dec. 1999; pp. 1461–1493.

Poncharal, Philippe et al.; *Electrostatic Deflections and Electromechanical Resonances of Carbon Nanotubes*; Science; vol. 283; Mar. 5, 1999; pp. 1513–1516.

Ren, Z.F. et al.; *Growth of a single freestanding multiwall carbon nanotube on each nanonickel dot*; Applied Physics Letters, American Institute of Physics; vol. 75, No. 8; Aug. 23, 1999; pp. 1086–1088.

Reulet, B. et al.; *Acoustoelectric Effects in Carbon Nanotubes*; Physical Review Letters, The American Physical Society; vol. 58, No. 13, Sep. 25, 2000; pp. 2829–2832.

Roukes, M.L.; *Nanoelectromechanical Systems*; Technical Digest of the 2000 Solid–State Sensor and Actuator Workshop; pp. 1–10.

Routkevitch, Dmitri et al.; *Nonlithographic Nano–Wire Arrays: Fabrication, Physics, and Device Applications*; IEEE Transactions on Electron Devices; vol. 43, No. 10; Oct. 10, 1996; pp. 1646–1658.

Schmalzing, Dieter et al.; *Toward Real–World Sequencing by Microdevice Electrophoresis*; Genome Research; vol. 9; pp. 853–858 1999.

Soper, Steven A.; *Nanoliter–scale sample preparation methods directly coupled to polymethylmetharcrylate–based microchips and gel–filled capillaries for the analysis of oligonucleotides*; Journal of Chromatography A; vol. 853; 1999; pp. 107–120.

Turner, S.W. et al.; *Monolithic nanofluid sieving structures for DNA manipulation*; J. Vac. Sci. Technol., American Vacuum Society; vol. 16, No. 6; Nov./Dec. 1998; pp. 3835–3840.

Van Der Gaag, B.P. et al; *Microfabrication below 10 nm*; Appl. Phys. Lett, American Institute of Physics; vol. 56, No. 59; Jan. 5, 1990; pp. 481–483.

Volkmuth, W.D. et al.; *DNA Electrodiffusion in a 2D Array of Posts*; Physical Review Letters, The American Physical Society; vol. 72, No. 13; Mar. 28, 1994; pp. 2117–2120.

Volkmuth, W.D. et al.; *DNA electrophoresis in microlithographic arrays*; Nature; vol. 358; Aug. 13, 1992; pp. 600–602.

Westermeier, Reiner; *Electrophoresis in Practice, A Guide to Method and Applications of DNA and Protein Separations, Chapter I—Electrophoresis*; Second Edition; VCH, a Wiley company; 1997; pp. 6–39.

Wildöer, Jeroen W.G. et al.; *Electronic structure of atomically resolved carbon nanotubes*; Nature; vol. 391; Jan. 1, 1998; pp. 59–62.

Xu, Yan; Capillary Electrophoresis; Analytical Chemistry, American Chemical Society; vol. 71, No. 12; Jun. 15, 1999; pp. 309R–313R.

Yoon, Dy et al.; *Comparison of chain conformations for ploystyrene and model molecules in the gas phase, solvents and melts from MD simulations*; Abstracts of Papers, Part 2; 215th ACS National Meeting; American Chemical Society; Mar. 29–Apr. 2, 1998, 1 p.

Yu, Min–Feng et al.; *Tensile Loading of Ropes of Single Wall Carbon Nanotubes and their Mechanical Properties*; Physical Review Letters, The American Physical Society; vol. 84, No. 24; Jun. 12, 2000; pp. 5552–5555.

Zhang, Y. et al.; *Elastic Response of Carbon Nanotube Bundles to Visible Light*; Physical Review Letters, The American Physical Society; vol. 82, No. 17; Apr. 26, 1999; pp. 3472–3475.

Zhang, Yuegang et al.; *Electric–field directed growth of aligned single–walled carbon nanotubes*; Applied Physics Letters, American Institute of Physics; vol. 79, No. 19; Nov. 5, 2001; pp. 3155–3157.

Zhang, Y et al.; *Formation of single–wall carbon nanotubes by laser ablation of fullerenes at low temperature*; Applied Physics Letters, American Institute of Physics; vol. 75, No. 20; Nov. 15, 1999; pp. 3087–3089.

PCT International Search Report dated Mar. 14, 2002 from corresponding PCT application No. PCT/US01/06035 filed Feb. 22, 2001.

Duke, Thomas et al.; *Sequencing in nanofabricated arrays: A feasibility study*; Electrophoresis; 1997; vol. 18; pp. 17–22.

Korgel, Brian A. et al.; *Self–Assembly of Silver Nanocrystals into Two–Dimensional Nanowire Arrays*; Advanced Materials; 1998; vol. 10, No. 9; pp. 661–665.

Li, J. et al., *Highly–ordered carbon nanotube arrays for electronics applications*; Applied Physics Letters, American Institute of Physics; Jul. 19, 1999; vol. 75; pp. 367–369.

* cited by examiner

DEVELOPMENT OF A GEL-FREE MOLECULAR SIEVE BASED ON SELF-ASSEMBLED NANO-ARRAYS

CROSS-REFERENCE TO RELATED APPLICATION

This application is based on U.S. Application No. 60/184,201, filed Feb. 22, 2000, the disclosure of which is incorporated by reference.

STATEMENT REGARDING FEDERALLY SPONSORED RESEARCH

The U.S. Government has certain rights in this invention pursuant to grant No. NAS 7-1407, awarded by the National Aeronautics and Space Administration, Office of Space Science.

FIELD OF THE INVENTION

The present invention is directed to a self-assembled nano-array molecular sieve for the separation of molecules.

BACKGROUND OF THE INVENTION

This invention relates in general to self-assembled nanometer-scale arrays used as molecular sieves in the separation of molecules by differential transport through the array, and in particular to self-assembled carbon nanotube arrays used as electrophoretic sieves for DNA sequencing and separation of biological molecules comprising a self-assembled carbon nanotube array arranged on a substrate and an electromagnetic field generator for applying a potential across the array sieve producing a characteristic mobility in the molecules.

Electrophoresis is the predominant technique for separating DNA fragments obtained from restriction maps of complete genomes (millions of base pairs long) and for large-scale sequencing projects, like the Human Genome Initiative. Electrophoresis has also become an essential tool for clinical chemistry applications. In conventional electrophoretic sieves, electrophoretic separation occurs by differential transport of polyelectrolytes, such as, DNA molecules and proteins, through a medium or device in the presence of an electric field. The medium acts as a sieve, producing a size-dependent mobility in the molecules. In slab gel electrophoresis, the sieving medium is provided by a slab gel of agarose or polyacrylamide polymers, which contain nanometer-size pores. For example, an agarose gel is made by placing agarose into solution with a suitable solvent and the pore size depends on the concentration of agarose in solution according to the equation:

$$a \approx 89 \cdot A^{-2/3} \text{ nm} \quad (1)$$

where a is the pore size and A is the concentration of the agarose in (g/mL). Pore size for an agarose gel with A~0.1 to 1.0 g/mL is in the range of 100 to 500 nm.

Polyacrylamide polymers are produced through a polymerization reaction of acrylamide and methylenebisacrylamide. By controlling the conditions of the reaction, such as acrylamide concentration and the degree of cross-linking, the pore structures thus formed can be reproducibly controlled and can have pore sizes as small as a few nanometers. Because of the small pore size, polyacrylamide gel electrophoresis (PAGE) is the method of choice for separating small DNA strands (<1000 bases) for DNA sequencing or genetic mutation studies, such as cancer detection or toxicology.

Despite the wide-range of pore sizes available, and the well-documented reproducibility of the conventional gel electrophoresis techniques, severe throughput limitations, size limitations and the need for cleaner, hardier and more user-friendly technologies have led a number of researchers to look for ways to improve the automation and rapidity of electrophoretic techniques. For example, sequencing speed is limited in gel electrophoresis because the electric fields used to push the molecules through the sieve must be kept low to avoid Joule heating of the gel, which could cause degradation of the gel material. In addition, gels are not very durable, requiring constant replacement which results in the further requirement for extra-plumbing and reservoirs to allow facile replacement of the gel adding to both the size and complexity of the gel-electrophoresis equipment.

One recent advance has been capillary electrophoresis (CE). In capillary electrophoresis, a small diameter capillary acts as the sieve for the molecules. CE has gained widespread popularity because the small-scale CE sieve structures allow for the facile dissipation of excess heat, which in turn allows for the use of higher electric fields resulting in a reduction in sequencing time. However, CE systems still contain gels and would thus not be appropriate for extended periods of use, because of the added complexity of storing replaceable gels and injecting them periodically in the micro-channel structure.

Hybridization techniques have offered some promise for rapid separation. However, technical issues in data collection, such as low signal-to-noise ratios and analysis, such as computationally intensive combinatorial analysis have prevented hybridization techniques from becoming the standard in DNA analysis.

More recently, researchers at Princeton have introduced micro-fabricated arrays as artificial sieving structures to replace polymer-based sieves. These artificially fabricated arrays have several advantages compared to both the polymer gels and the capillaries including: 1) the possibility of using ultra-high fields enabling higher speed separation and real-time monitoring of DNA samples; 2) the use of a non-viscous medium leading to higher durability and which in turn could possibly lead to the development of permanent sieves; 3) the flexibility and controllability of the configuration of the sieving structure would allow for analysis over a broad range of molecular sizes, from simple DNA fragments to full chromosomes, and the production of devices on a very large scale for parallel processing; 4) because these structures can also be fabricated with extremely regular sized and spaced sieve features, the separation resolution should be improved leading to further miniaturization of the electrophoresis device, including the possibility of an electrophoresis analyzer on a chip; and 5) because the sieves can be built from inert substances analysis can be made of a variety of biomolecules.

One example of a micro-fabricated array formed using ion-beam lithography was disclosed by Duke et al., in *Electrophoresis*, vol. 18, pages 17–22 (1997), incorporated herein by reference. Duke et al. produced a periodic array of pillars 100 nm in diameter and 100 nm apart and demonstrated the ability to differentiate the electrophoretic mobility of DNA molecules between 7.2 and 43 kilobases (kb). Other disclosures of lithographically produced arrays for the use in electrophoresis devices are described in U.S. Pat. Nos. 5,110,339 and 5,837,115, both of which are incorporated herein by reference.

While this method clearly shows promise for providing nano-scale array sieves for separating DNA molecules having several thousand base pairs, the lower limit for array features made using such lithographic techniques is about 100 nm, indicating that smaller DNA molecules cannot be separated. Moreover, due to the time-intensive nature of e-beam lithography, it is not suitable for the economical fabrication of large dense arrays of with pore sizes approximately below 50 nm. This in turn limits the application of such sieves to DNA separation but not sequencing, which requires the separation of DNA molecules as small as a few base pairs long. In order to provide separation of molecules of up to 600 bases, inter-post separations of approximately 15 to 30 nm will be needed. Moreover, despite the progress made in recent years in developing new techniques to produce smaller and smaller features via lithographic techniques such as ion beam or electron beam lithography, it is clear that increasingly costly efforts are being required to sustain the progress. While deep UV and X-ray lithography offer hope of incremental improvements in resolution, lithographic and patterning techniques for reproducibly producing features at the 10 to 30 nm level are essentially nonexistent at the present time. The resolution limit of currently available patterning technologies make it apparent that entirely new approaches will be needed to sustain the rapid progress that has characterized the last few decades of semiconductor technology development.

One novel approach to making nanometer-scale structures utilizes self-assembly of atoms and molecules to build up functional structures. In self-assembled processing, atom positions are determined by fundamental physical constraints such as bond lengths and angles, as well as atom-to-atom interactions with other atoms in the vicinity of the site being occupied. Essentially, self-assembly uses the principles of synthetic chemistry and biology to "grow" complex structures from a set of basic feedstocks. Utilizing such techniques molecular motors have been synthetically produced containing fewer than 80 atoms. Two relatively simple examples of self-assembled structures formed using chemical vapor deposition (a process commonly used in thin film deposition, including crystal-growth) include carbon fullerenes ("buckyballs") and carbon nanotubes. In addition, dense arrays of carbon nanotubes have been grown on surfaces and such arrays have been utilized as nano field emitter arrays, atomic force microscopy probes, nanoscale transistors, actuators, high-Q mechanical resonators and a variety of sensors.

While fabrication processes based on self-assembly at the nanometer scale have a number of advantages over the conventional lithography techniques, including avoiding the blanket film depositions, lithography, and subtractive processing characteristic of conventional nano-scale manufacturing, until recently there has been no method based on self-assembly for fabricating uniform nano-arrays of the type necessary to build an instrument for electrophoretic separation. Instead, the nano-arrays formed have been disordered on a fine scale with uncontrolled spacing between individual nanotubes and a significant spread in nanotube diameters.

Recently, a technique has been developed that relies on self-assembly to produce geometrically regular nanotube arrays with excellent uniformity. This process is based upon the self-organizing formation of highly uniform pore arrays in anodized aluminum films. First, a nanochannel alumina structure is formed by anodizing an aluminum film under conditions that lead to hexagonally-ordered arrays of narrow channels with very high aspect ratios. The nanochannel alumina structure is then used as a template for the growth of nanotube arrays of carbon and other materials, including metals and some semiconductors. The full process technique is disclosed in *Appl. Phys. Lett.*, vol. 75, pg 367 (1999), and is incorporated herein by reference. Utilizing this technique the authors were able to grow nanotube arrays comprising uniform carbon nanotubes with a diameter of 32 nm. Despite the promise of this new technique, there have been no attempts to adapt the technology to grow array structure capable of being used as an electrophoretic sieve for analyzing and sequencing DNA and RNA.

Accordingly, a need exists for a durable non-gel sieving device capable of analyzing a wide range of molecular sizes under the influence of ultra-high electric fields and capable of being produced on a large scale for parallel processing.

SUMMARY OF THE INVENTION

The present invention is directed to a device and system for utilizing a non-gel self-assembled nano-array molecular sieve for analyzing biomolecules. In one particular embodiment this invention utilizes a non-gel ordered self-assembled array of nano-features that functions as an electrophoretic sieve to separate biomolecules. This invention is also directed to systems for integrating the non-gel ordered self-assembled nano-array sieve of this invention into a device for separating biomolecules. This invention is also directed to novel methods for separating a wide range of biomolecules using the non-gel ordered self-assembled nano-array sieve of the invention.

In one embodiment, the self-assembled nano-array of the present invention is incorporated into an electrophoretic micro-device comprising a self-assembled nano-array according to the present invention, a field generator for applying an electric field across the sieve, and a detector. The self-assembled nano-array sieve is designed to differentially transport polyelectrolytes, such as DNA molecules, proteins, etc., through the sieve in the presence of an electric field to produce a characteristic distribution of the introduced molecules. The nano-array is placed in line-of-sight with the detector such that as the molecules exit the sieve, they flow through the optical detection region of the detector. The detector then analyzes the exiting molecules such that the identity of the exiting molecule can be determined.

In one embodiment, the self-assembled nano-array sieve comprises a substrate having a periodic array of features such that in the presence of an appropriate feedstock the atoms of the feedstock self-assemble on the ordered features of the substrate to produce an ordered array of nano-features having non-random alignment and size distribution. In one embodiment the size, shape and pattern of the self-assembled nano-array features grown on the substrate are adapted such that molecules within a specified size range can be separated. The substrate wafer is preferably made of a substance that reacts with the feedstock to produce the self-assembled structures.

In another embodiment the nano-array features self-assemble into nanotubes having a specified diameter and height suitable for use in the sieve of the current invention.

In an alternative embodiment, the substrate is made of a semiconductor such as, for example, oxidized silicon or aluminum oxide, coated with a metal catalyst film such as, for example, Ni or Co. In this embodiment, the silicon can be further doped to adjust the electronic properties of the substrate surface.

In another alternative embodiment, the self-assembled nano-array sieve is confined in a channel and the outer surface of the array optionally covered with a cap layer so as to enclose the nano-array sieve such that the DNA molecules are confined within the sieve during separation. In such an embodiment, either the cap layer or the substrate must be transparent to light such that optical detection schemes can be utilized to analyze the molecular distribution. In this embodiment, reservoirs can be integrated into the channel and cap to provide an entrance point for the molecules to be tested.

In another alternative embodiment, the nano-array features are self-assembled from an inert material such as, for example, carbon utilizing a carbon feedstock gas such as, for example, acetylene.

In yet another alternative embodiment, the detector comprises a laser induced fluorescence system such as, for example, a laser diode emitter in conjunction with a binary superimposed grating, or conventional optics and a photomultiplier tube.

In still another alternative embodiment, the electrophoresis system of the present invention is utilized in combination with a DNA sequencer. In such an embodiment, the DNA strands would be labeled with a specific dye for each of the chain-terminating dideoxynucleotides and a binary superimposed grating in conjunction with four spatially separate optical detectors would be utilized to determine the identity of the tested molecules. In this embodiment, preferably the carbon nanotube array would have a pore size of about 15 nm and the molecules would have a size up to about 1,000 bases long.

In still yet another alternative embodiment, the invention is directed to a system for the detection of substances comprising multiple sieve paths and detectors as described above, such that parallel processing of molecules can be carried out.

In still yet another additional embodiment, the invention is directed to a method for separating molecules based on molecular size. The method comprises analyzing molecules introduced into the self-assembled nano-array sieve as described above.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
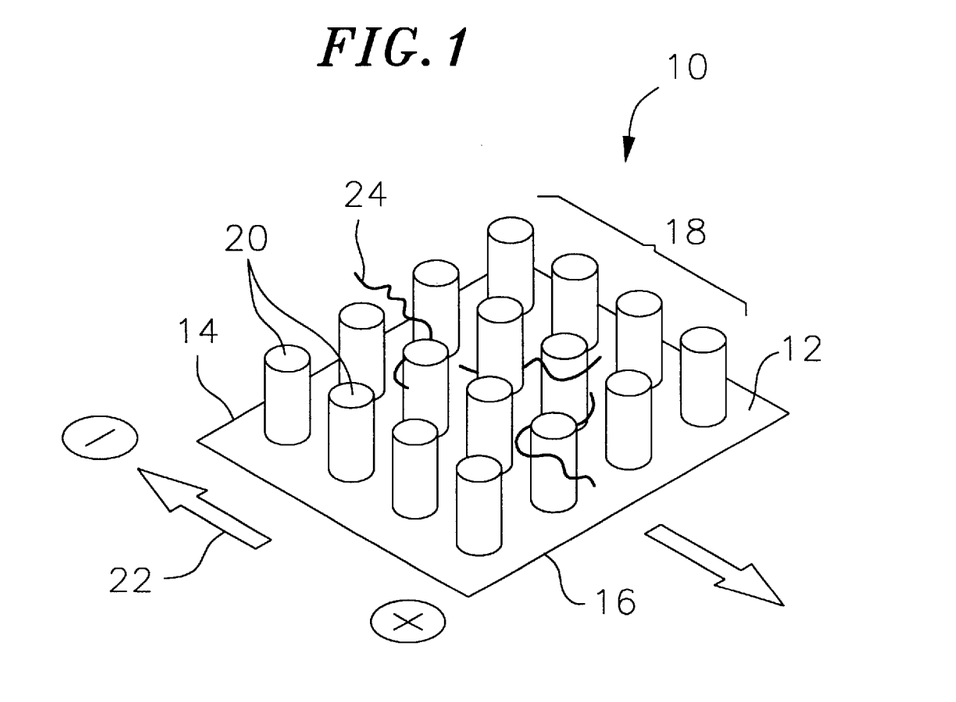
FIG. 1 is a schematic view of an embodiment of a nano-array sieve according to the invention.

The present invention is directed to a molecular sieve instrument comprising a non-gel self-assembled nano-scale periodic array sieve for discriminating molecules based on a characteristic mobility. As shown in FIG. 1, the molecular sieve 10 comprises a substrate 12 having proximal 14 and distal ends 16 and an array 18 of self-assembled nano-features comprising an ordered repeating pattern of nano-features 20 arranged on the substrate 12 of the molecular sieve 10. In operation, an electric field 22 is applied across the length of the array 18 from the proximal 14 to the distal 16 end such that molecules 24 introduced onto the array 18 surface move through the array 18 to a detector (not shown) in a time dependent on a characteristic of the molecule 24, such as, for example size, charge, chemical inertness, etc.

Although in the embodiment shown in FIG. 1, the self-assembled array 18 of nano-features comprises periodic rows of uniform nano-features 20 attached to the substrate 12, any other arrangement of nano-features 20 suitable to function as a molecular sieve 10 can be utilized such as, for example, staggered arrays of uniform nano-features or uniform rows of nano-features having alternating sizes. In another alternative embodiment the spacing of the nano-features 20 is varied to produce a gradient gel for which sieving properties vary spatially. Additionally, while FIG. 1 only shows a molecular sieve 10 deposited on a flat substrate surface 12, any geometry of substrate 12 suitable for use as a molecular sieve 10 could be utilized, such as, for example, a curved, corrugated or tubular substrate. It will be understood that the design of the molecular sieve 10 according to the present invention is necessarily driven by the molecules 24 to be separated as the sieving ability of the molecular sieve 10 is sensitively dependent on both the geometrical size, shape and spacing of the nano-features 20 as well as the size and properties of the molecules 24. The molecular sieve 10 itself has two characteristic sizes: (1) the nano-feature size and (2) the nano-feature spacing, or pore size. Using an iterative process, the nano-features 20 can be optimized to separate molecules 24 of a specified size or other physical property, then other parameters can be selected to optimize operation, such as, for example, electric field 22 strength, detector and the mechanical properties of the sieve body. Accordingly, although the self-assembled molecular sieve 10 of the embodiment shown in FIG. 1 comprises a uniform array 18 of uniform cylindrical nano-features 20, it should be understood that any shape, size or spacing of nano-features 20, as described above, can be utilized in the molecular sieve 10 of the current invention such that the pore size and sieving properties of the array 10 are suitable for use as a separation device for the molecules 24 of interest.

For example, a sieve must possess specific properties to separate double strand DNA (dsDNA) and single strand DNA (ssDNA) molecules. The DNA molecule generally appears in its dsDNA configuration. The dsDNA molecule can span a wide variety of sizes, ranging from a few kilo-base-pairs (kbp) to many Mbp, such as, for example, chromosomes. To provide sequencing capabilities, on the other hand, the molecular sieve 10 must be able to process ssDNA molecules which are produced by Maxam-Gilbert or Sanger sequencing reactions. In contrast to the dsDNA molecule, the ssDNA molecule used for sequencing is typically no more than 1,000 bases long. Accordingly, the design of a molecular sieve 10 intended to separate either form of DNA requires that the conformational behavior of ssDNA and dsDNA under electrophoresis be known. This behavior, in turn, strongly relies on the physical properties of the array 18 and sieve 10. For example, if the gaps or pores between the nano-features 20 in the arrays 18 are smaller than 30 nm, pulsed electrophoresis utilizing a pulsed electric field 22, which requires the bending of DNA, may not be feasible because of the minimum bending diameter of dsDNA ($D_b$~30 nm). Also, the value of the electric field 22 E compared to the electric field $E_0$ required to balance the thermal motion of Kuhn segment will influence the stretching configuration of the molecules 24. The relaxation time, or Rouse time $T_R$, associated with the molecules may also impose a limit on the design dimensions of a molecular sieve 10 for sequencing. Table 1, below, compares the physical properties of the ssDNA and dsDNA molecules.

TABLE 1

Properties of dsDNA and ssDNA

| Property | ssDNA | dsDNA |
| --- | --- | --- |
| Nucleotide length (n) | n bases | n base pairs |
| Persistence length (p) | ~0.75 nm | ~50 nm |
| Kuhn length (b) | 1.5 nm (~3 bases) | 100 nm (~300 base pairs) |
| # Kuhn segments (N) | ~n/3 | ~n/300 |
| DNA contour length (L) | N · b<br>~500 nm (n~1 kb) | N · b<br>~30 μm (n~100 kbp) |
| Random coil gyration radius ($R_g$) | ~$N^{3/5}$ · b<br>~50 nm (n~1 kb) | ~{⅓ · p · L · [1 − p/L + p/L · $e^{-L/p}$]}$^{1/2}$<br>~700 nm (n~100 kbp) |
| Minimum bending diameter ($D_b$) | ~0.50 nm | ~30 nm |
| Charge/Kuhn length (q) | −1 e | −50 e |
| Friction coefficient/Kuhn segment (ζ) | 8 · $10^{-12}$ kg/s | 4 · $10^{-10}$ kg/s |
| Electrophoretic mobility ($\mu_0$ = q/ζ) | 2 · $10^{-8}$ m$^2$/s · V | 2 · $10^{-8}$ m$^2$/s · V |
| Electric field strength to balance thermal motion at T~25° C. ($E_0$ = k · T/q · b) | $10^5$ V/cm | 50 V/cm |
| Time associated with Brownian motion of Kuhn segment at T~25° C. (τ = ζ · $b^2$/k · T) | $10^{-8}$ s | $10^{-3}$ s |
| Rouse time ($T_R$ = τ · $N^2$/(3 · $\pi^2$)) | $10^{-5}$ s<br>(n~1 kb) | 1 s<br>(n~100 kbp) |

Figure 2:
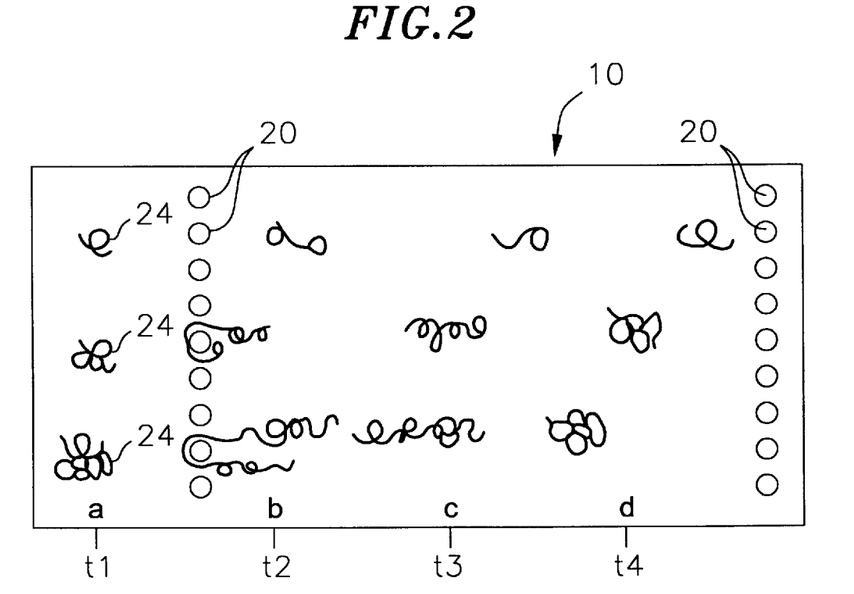
FIG. 2 is a schematic view of an embodiment of a nano-array sieve in operation according to the invention.

A schematic diagram of the mechanism of separation in a molecular sieve 10 is shown in FIG. 2. Three DNA molecules 24a, 24b, and 24c, are pictured at even time intervals (t1 to t4), as they migrate through a row of nano-features 20 in a molecular sieve 10. The longest molecule 24c is most hindered by the interaction with the nano-features 20 and is consequently the last to arrive at the next row. The reason for this demonstrated behavior is that molecules 24 having different sizes relative to the pores between the nano-features 20 in the array sieve 10 interact with the nano-features 20 differently. For randomly coiled molecules whose gyration radius is smaller than the pore size 26 of the self-assembled molecular sieve 10, such as for molecule 24a, sieving, also called Ogston-sieving, occurs and the migration speed is dependent on the gyration radius of the molecule 24a. For larger strands (such as the DNA molecules 24b and 24c), the molecules need to uncoil to fit through the pores, as shown at t2. To overcome this limitation, the electric field 22 can be increased to allow stretching of the molecules 24 to occur. Under the influence of the electric field 22, the molecule 24b then reptates though the pores with snake-like movement and the migration speed is dependent on molecular size up to a given size. However, there is an upper limit to the effectiveness of uniform array sieves. For example, at higher electric fields or for longer strands, molecules wrap themselves around the nano-features 20, as shown for molecule 24c at t2, with both sides of the molecule 24c hanging on either side of the nano-feature 20 under the tension of the electric field 22. In molecular sieve 10, such as that shown in FIG. 1, molecules 24 slide or hook around the nano-features 20 as in a pulley system, thus freeing the molecules 24. This episodic "hooking", unlike reptation or Ogston sieving, does not segregate between molecular sizes in uniform arrays, and does not appear to be an effective sieving mechanism. Likewise, at very high fields, DNA molecules 24 are fully-stretched and slide through the nano-features 20 unperturbed because of the regularity of the sieve 10 (a phenomenon absent in gels because of the randomness of the sieving structure). Accordingly, if a sieve 10 is made having gaps, or pores, 26 between nano-features 20 of 15 nm, the maximum length of the molecule 24 that would obey the Ogsten sieving regime would be n~50 bases, while for molecules 24 longer than 50 bases, reptation or even hooking might occur. Such physical limitations can be overcome by using staggered arrays, as shown in FIG. 2 or by pulsing a second electric field 28 at a field vector angled in relation to the vector of the driving electric field 22. Accordingly, the design of the molecular sieve 10 as well as the operating conditions of the electric field 22 will depend on the size and size range of the molecules 24 to be separated.

While the self-assembled nano-arrays 18 contemplated in many of the embodiments discussed in the present application are constructed of carbon nanotube nano-features 20 made from pyrolizing an acetylene feedstock over a substrate having an ordered array of germination points, the nano-features 20 can be of any shape and made by any process and from any material suitable for making self-assembled nano-features, such as, for example, spheres or pyramids made of other atomic materials or even biomolecules, such as, for example, proteins. In another embodiment, the nano-features 20 are further functionalized for a variety of applications, such as, for example, being made hydrophilic or hydrophobic, being charged either negatively or positively, or being derivatized with specific chemical groups, etc.

The substrate 12 can be made of any material which can withstand the temperatures required for growth of the nano-features 20 and which can be modified to provide a suitable ordered array of germination points for growing the nano-features 20 of the array 18, such as, for example, metallized Si oxide wafers, anodized alumina, glass, or even polymeric plastics. In turn, any suitable catalyzing metal can be used to activate the germination points on the surface of the substrate 12, such as, for example, nickel or cobalt. Alternatively, the catalyzing metal could be an alloy of two or more metals such as a Co/Ni alloy. The metal catalysts could also be produced by pyrolysis of inorganic or organic metal-containing compounds, such as, for example, Ferric Nitrate or Cobalt Chloride.

Figures 3A, 3B, 3C, 3D:
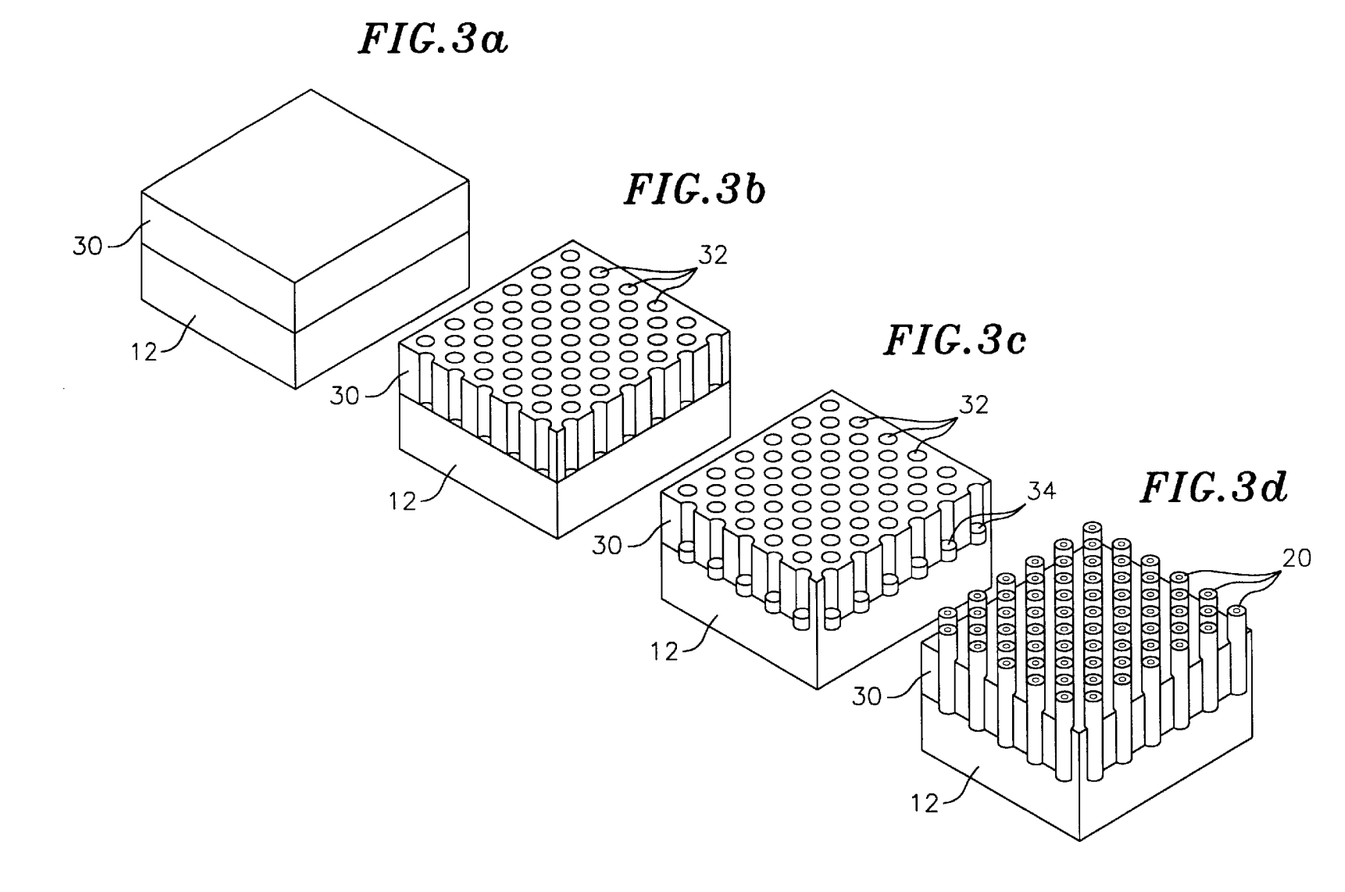
FIG. 3a is a schematic view of an embodiment of a process for forming a nano-array sieve according to the invention.
FIG. 3b is a schematic view of an embodiment of a process for forming a nano-array sieve according to the invention.
FIG. 3c is a schematic view of an embodiment of a process for forming a nano-array sieve according to the invention.
FIG. 3d is a schematic view of an embodiment of a process for forming a nano-array sieve according to the invention.

One possible process for forming the molecular sieve 10 of the present invention comprising nanotube nano-features 20 utilizing a chemical vapor deposition (CVD) technique is shown schematically in FIGS. 3a to 3d. In a first step, as shown in FIG. 3a, a substrate 12, such as, for example, silicon is coated with a high purity metal film 30, such as, for example, Al. The metal is then anodized in a multistep process to produce germination points or pores 32 in the highly ordered sieve array 18 in the metal oxide surface 30, as shown in FIG. 3b. Next, a small amount of catalytic material 34, such as, for example, Co or Ni is electrochemically deposited in the bottom of the pores 32 to serve as a catalyst for carbon nanotube nano-feature 20 growth, as shown in FIG. 3c. Finally, as shown in FIG. 3d, the nanotube nano-features 20 are self-assembled by pyrolysis of a suitable feedstock, such as, for example, acetylene gas diluted in nitrogen and/or ammonia at about 650° C. and the nanotube nano-features 20 then partially exposed by etching the metal oxide film 50 in a mixture of phosphoric and chromic acids. The anodized surface 30 and the catalyzed pores 32 serve as a template such that the nanotube nano-features 20 self-assembled in an ordered array 18 corresponding to the pores 32 in the anodized metal substrate 30. A detailed description of this method for the self-assembled growth mechanism of a well-ordered self-assembled carbon nanotube array is found in, *Appl. Phys. Let.* vol. 73, page 3845 (1998), which is incorporated herein by reference.

Figure 4:
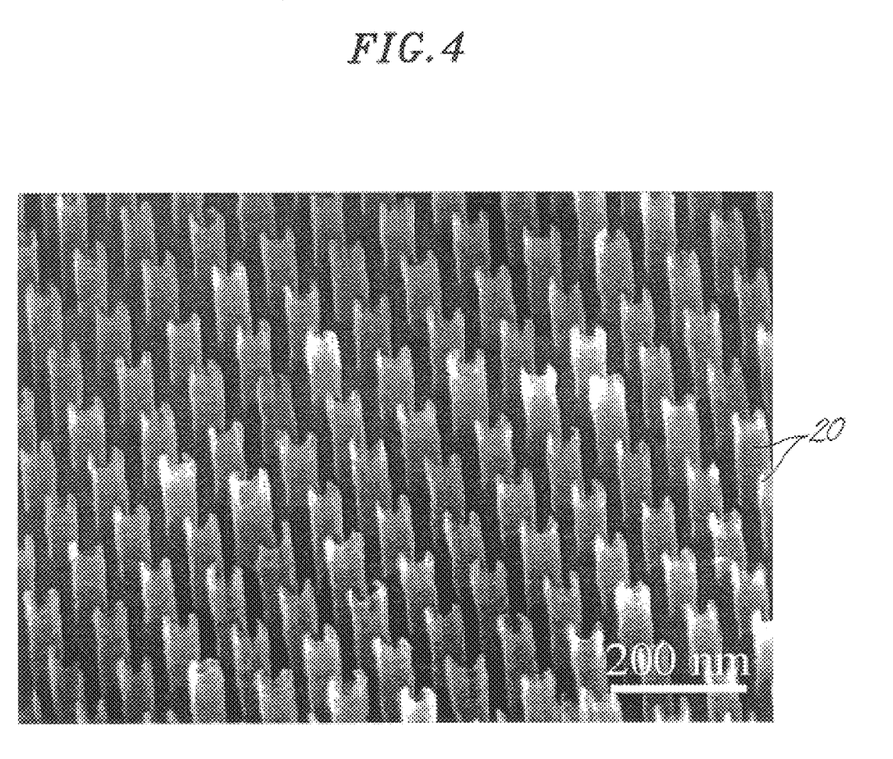
FIG. 4 is an SEM image of an embodiment of a nano-array sieve according to the invention.

FIG. 4 is an SEM micrograph of a self-assembled nano-array 18 comprising nanotube nano-features 20 produced by this process. As shown, utilizing this technique, nanotube nano-features 20 of uniform length and cross section and with only a 5% spread in diameter can be grown in very regular hexagonal arrays of parallel nanotubes. Moreover, the relatively low vapor deposition growth temperature makes the technique compatible with basic Si processes. Furthermore, because the pore diameter is proportional to the anodization voltage, the pore size can be controlled from 10 nm up to several hundred nm with nano-feature areal densities as high as $10^{11}$ cm$^{-2}$. Voltage control of the nanochannel diameter also offers the possibility of optimizing the nano-feature diameter for sieving molecules with different baselengths.

Determination of an appropriate shape, size and spacing of self-assembled nano-features 20 for a specific molecular sieve 10 can be determined via any traditional theoretical electrodynamic calculation method. The description and modeling of polyelectrolytes (e.g., DNA, RNA and almost every protein) is difficult due to the competing interaction of short and long range interactions, which introduce new length scales and new degrees of freedom to the well understood concepts of neutral polymer physics. Techniques must take into account both the interplay of various length scales inherent to systems of polyelectrolytes and also in the different regimes of concentrations of chains, but also the crucial role of screening interactions of polyelectrolytes by the counter-ions and salt ions in solution.

Suitable simulations may employ potential functions for the short-range interactions, such as, for example, Lennard-Jones field, multibody interactions (Morse-type potentials), bonded interactions and for the long-range electrostatic interactions. Such molecular dynamics simulations may use any combination of conventional algorithms, such as, for example, (a) the Nose-Hoover algorithm for constant pressure and constant temperature systems; (b) optimized or non-optimized interpolation Particle-Particle-Particle-Mesh and multiple algorithms with tree data structures for the treatment of the long range electrostatic potentials in periodic and non-periodic systems; and (c) efficient domain decomposition techniques that allow for efficient parallelization for short-range forces. Multiple steps for the integrations can also be utilized to model separate time scales. Simple multibead-spring models, which can be mapped onto realistic polymer and/or polyelectrolytes can be utilized as approximations to investigate chain conformations of polymer blends and polyelectrolyte solutions in various concentration regimes and in solvents of different quality such that the counter-ions and salt ions can be taken into account. Some examples of conventional modeling techniques that may be utilized include: the non-equilibrium molecular dynamics (NEMD) technique and the non-equilibrium Brownian dynamics (NEBD) technique. NEMD is a convenient and precise method to investigate the response of a complex fluid to an external, e.g. flow field. The NEMD technique is based on the numerical solution of Newton's equations of motion for many particle systems whose intermolecular potentials are given. NEBD and the "equivalent" Fokker-Planck equations treat the dissipative part of the NEMD motions in a less precise, but very efficient way.

Figure 5:
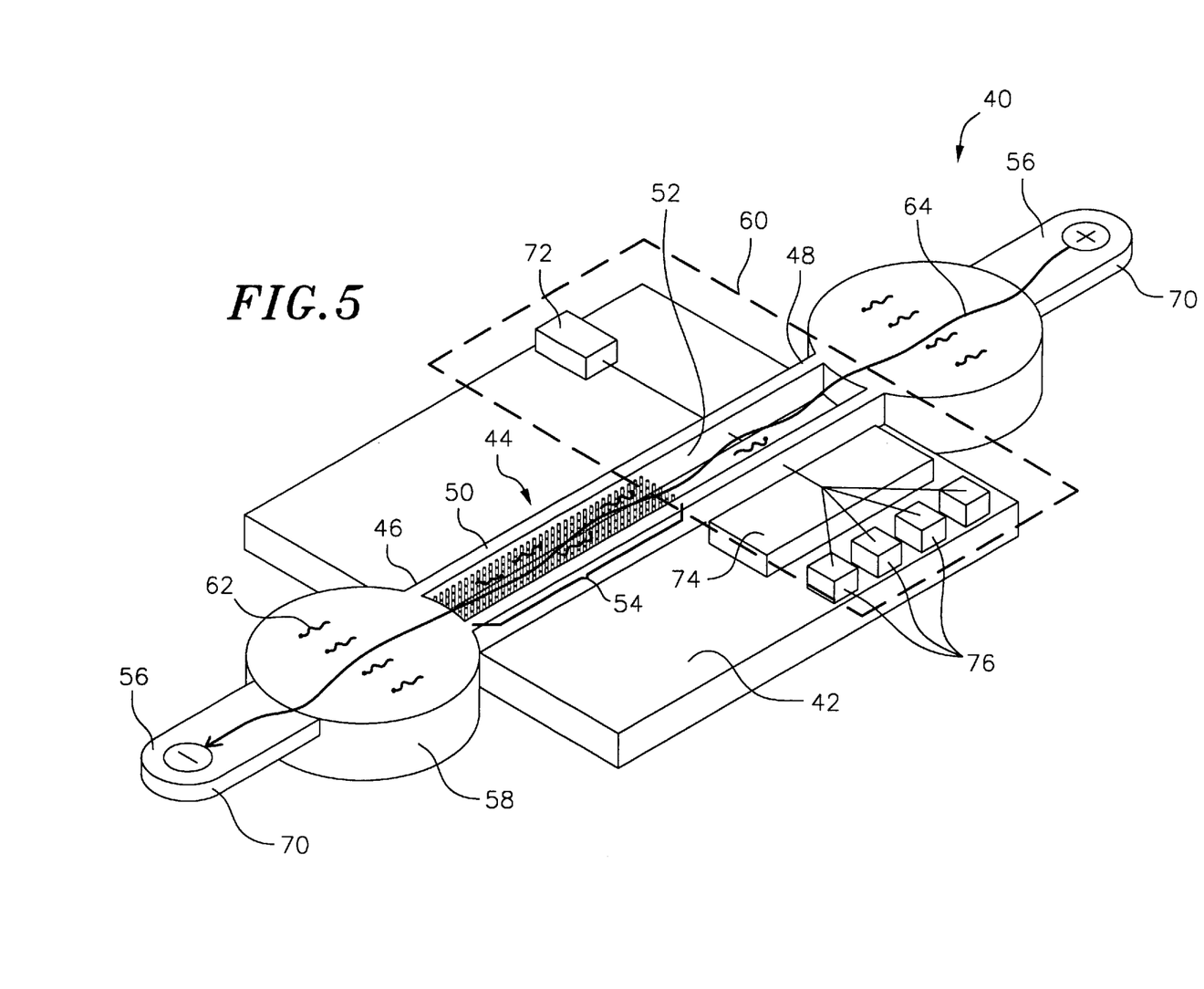
FIG. 5 is a schematic view of an embodiment of a molecular sieve device according to the invention.

In one embodiment, as shown in FIG. 5, the self-assembled molecular sieve 10 is incorporated in an electrophoretic instrument 40 which comprises a substrate 42, a sieve body 44 having proximal 46 and distal 48 ends and sieve walls 50 enclosing an internal volume 52, a non-gel self-assembled periodic nano-array sieve 54 arranged within the internal volume 52, an electric field generator 56 in field communication with the array sieve 54, a molecular reservoir 58 in fluid communication with the proximal end 46 of the sieve body 44 and a detector 60 in signal communication with the distal end 48 of the sieve body 44.

In operation, molecules 62 are placed into the molecular reservoir 58 and power is supplied to the electric field generator 56. The application of power to the electric field generator 56 produces an electric field 64 having a specified charge vector and strength. This electric field 64 is applied across the sieve 54 from the proximal 46 to the distal 48 end of the sieve body 44 such that the polyelectrolyte molecules 62 stored in the molecular reservoir 58 at the proximal end 46 of the sieve body 44 are induced to move through the sieve 54 from the proximal 46 to the distal end 48 of the sieve body 44 to the detector 60 under the influence of the electric field 64 at a rate dependent on a characteristic of the molecule 62, such as, for example, size. The detector 60 is arranged with the end of the sieve 54 such that molecules 62 passing out of the sieve 54 are analyzed by the detector 60. Utilizing this technique, sequencing with a 0.1% length resolution can be performed with self-assembled nano-array sieves 54 in a time of 100 seconds over a 10 cm sieve length. For separation based on conformation, full separation can be performed in seconds over a 1 cm array sieve 54.

The sieve body 44 itself can be made of any material suitable for micromachining utilizing standard lithographic or MEMS techniques to enclose the array sieve 54, such as, for example, aluminum oxide or silicon. In a preferred embodiment, the sieve body 44 further comprises a cap layer 66 which can be of any design such that the cap layer 66 makes intimate contact with the array sieve 54, while maintaining a uniform separation from the existing substrate 42. Such a cap layer 66 could be made of any suitable material, such as, for example, aluminum oxide or silicon. Such a cap layer 66 could be formed by any conventional MEMS process, such as growth or deposition over a sacrificial layer (not shown) deposited to encapsulate the self-assembled nano-array sieve 54 wherein the sacrificial layer is subsequently removed to expose the self-assembled nano-array sieve 54 itself. Alternatively, the cap layer 66 and channel 68 could be formed in a single deposition step with the self-assembled nano-array sieve 54 being embedded into the boundaries of the channel 68 such that alternative diffusion paths are avoided during electrophoresis. In a more preferred embodiment, one of the substrate 42, the cap layer 66, or sieve walls 50 is transparent such that an optical detector 60 can be used to interrogate the array sieve 54.

Figure 6:
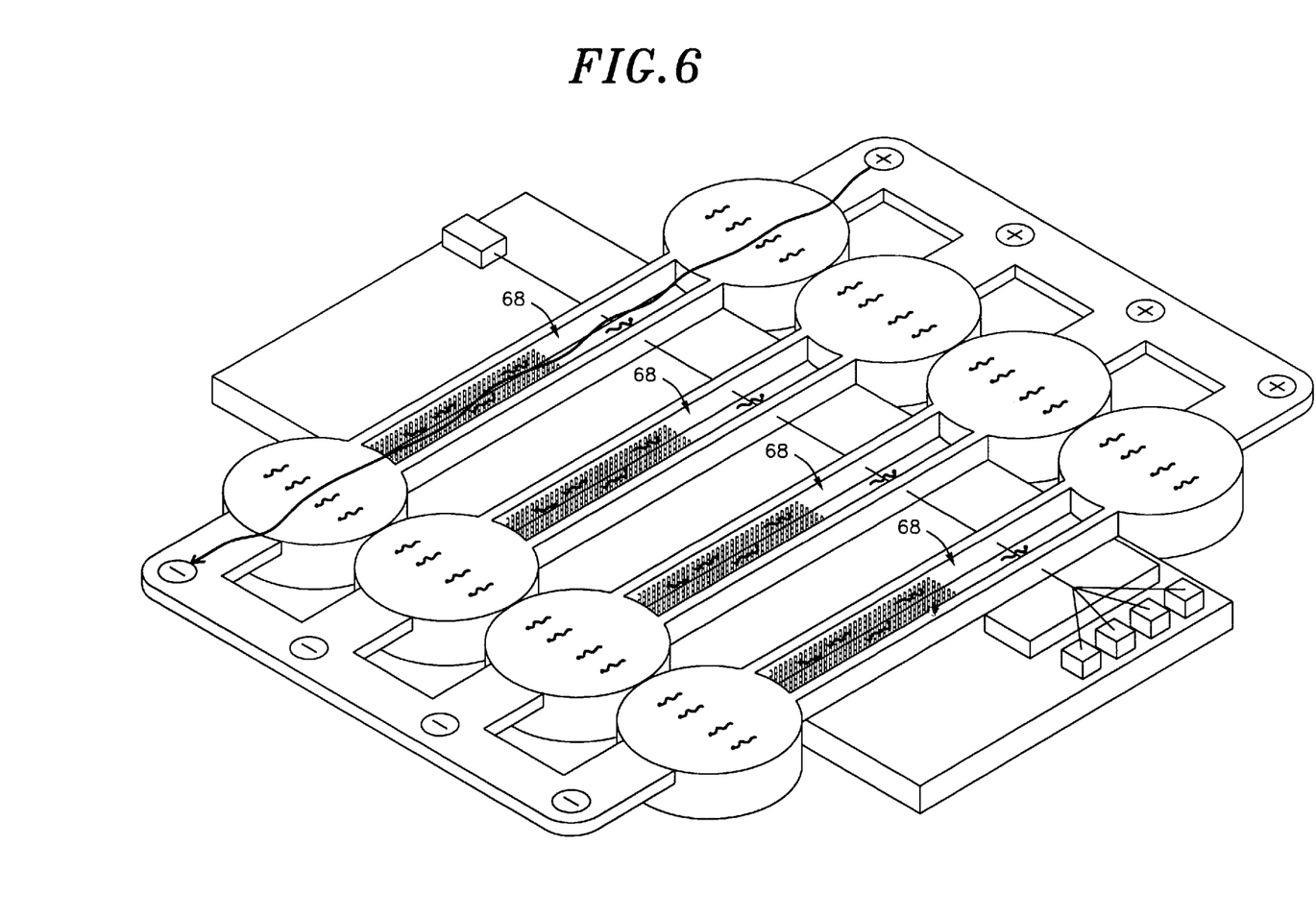
FIG. 6 is a schematic view of an embodiment of a molecular sieve device according to the invention.

Although the sieve body 44 shown in FIG. 5 comprises a single sieve 54 confined within a narrow channel 68, any geometry of sieve channels 68 can be utilized. One alternative embodiment is shown in FIG. 6, which shows a multiple channel sieve array 54 in which the array channels 68 are aligned in parallel on a single substrate 42 such that multiple or parallel processing of molecular samples can be carried out at one time. In this embodiment, multiple molecular reservoirs 58 are utilized for introduction of the molecules 62 to the sieve body 44. A single electric field generator 56 is utilized to apply a uniform across the entire array sieve 54. It should be understood that while parallel and single array channels 68 are shown in FIGS. 5 and 6, any suitable alternative geometry of channels 68 may be utilized such as, for example, folded channels may be used to increase the length of the sieve path 54 without increasing the size of the sieve body 44. Although the embodiment shown in FIG. 6 discloses a multi-channel array in which the sieve channels 68 are separated by sieve walls 60, the multi-channel array could alternatively comprise a single "sheet" of nano-array without walls between the array channels 68. In such an embodiment, the array channels 68 would be determined by the way the loading of the molecules 62 is performed because under the influence of the electric field 64, no significant lateral diffusion or intermixing of the samples should occur. For example, if loading can be achieved over a width of 0.5 mm, a substrate 12 1 cm on a side could hold 10 array channels 68, while if the array channel 68 width is only 50 μm, up to 96 array channels 68 could be included on a single substrate 12. Such an embodiment could be used to develop an electrophoresis device on a chip for mobile detection and analysis of samples. In such an embodiment a portable power source (not shown) would also be integrated into the device 40.

Although the above embodiments comprise open reservoirs 58 into which molecules 62 are injected, the molecules 62 can be introduced into the nano-array sieve 54 by any conventional technique dependent only on the narrowness of the array channel 68. For example, the molecules 62 could be stored in a thin slab of agarose gel which could then be positioned next to one of the edges of the array sieve 54. In such an embodiment, the molecules 62 would be released by application of the electric field 64. Alternatively, the apparatus could include means to inject molecular samples in narrow bands directly into the nano-array sieve 54. One potential technique is the gold wire technique in which a narrow strip of gold is used as a "starting line". Molecules 62 are bound to the gold by biasing the strip with a positive voltage. When the bias is switched off, the molecules instantaneously migrate away from the strip in a thin band. Another potential technique is electrokinetic injection, which allows for the introduction of single molecules into a sieve. This technique is disclosed in a number of published articles, such as, for example, *J. Chromatog. A.*, vol. 894, pg. 191–201 (2000), which is incorporated herein by reference.

The electrical field generator 56 can comprise any suitable generator such that an electromotive force is applied to the molecules 62 across the length of the sieve 54 via an electric field 64, such as, for example, positive and negative electrodes 70 in electrical contact with the proximal 46 and distal 48 ends of the sieve body 44. In such an embodiment, the electrodes could be made of any suitable conducting material, such as, for example, Al, Au or Ag. While a steady, uniform electric field 64 is contemplated in the embodiment described above, any suitable electric field 64 can be utilized, such as, for example, DC fields and pulsed fields. Additionally, any suitable electric field strength can be utilized such that sufficient separation of molecules can be obtained within a suitable timeframe. In a preferred embodiment, the field strength of the electric field 64 is between about 10 and 10,000 V/cm.

The detector 60, can comprise any suitable detection means such that the molecules 62 exiting the sieve can be monitored, such as, for example, a laser fluorescence spectrometer comprising a standard 488-nm laser source arranged such that the beam from the laser interrogates the distal end 48 of the array sieve 54 and the resulting fluorescence is collected by standard optics and photomultiplier tubes. Although the standard laser-induced fluorescence detector described above can be utilized for general separation and mobility analysis, in an alternative embodiment, a full DNA sequencing detector can be integrated into the device, utilizing four-color coding of the Sanger products. In such an embodiment, as shown schematically in FIGS. 5 and 6, the detector would comprise a light source 72, a binary superimposed grating 74 for multi-wavelength diffraction and a four element photodetector array 76. Alternatively, a single molecule detection technique for the imaging of individual molecules 62 could be utilized. In this embodiment a standard epi-fluorescence microscope with mercury lamp excitation and an inexpensive charge-coupled device (CCD) camera or alternatively an image intensified camera can be utilized to obtain time-resolved images. Suitable cameras are sold commercially by a number of manufacturers, such as, for example, the I-PentaMAX Gen IV Intensified CCD Camera sold by Roper Scientific.

In a preferred embodiment of the sequencing detector 60 described above, the light source 72 is a blue semiconductor light source emitting at a wavelength of 488 nm, the binary grating 74 is a binary superimposed grating composed of an array of equal sized pixels, each having two values in the index of refraction, spatially patterned according to a pre-programmed specific algorithm such that fluorescence emissions from the molecules 62 excited by the light from the light source 72 are separated based on the wavelength of the emission. In operation, during a Sanger reaction, the DNA molecules 62 are labeled with a specific dye for each of the four reactions in the presence of a chain-terminating dideoxynucleotides. In this manner, a particular dye is associated with a particular base (Adenine, Thymine, Cytosine or Guanine). Accordingly, when light from the light source 72 impinges on the molecules 62, an emission with a wavelength based on the specific chemistry of the dye will be emitted. The emission from the molecules 62 is then focused on the binary grating 74, which separates the four different wavelengths of the emission light and focuses the emission onto one of four spatially separated detectors 76. The output of each detector 76 is then monitored as a simple binary data stream to determine whether there is an input signal or not. A further discussion of the above technique is disclosed in *IEEE Photonic Tech. L.*, vol 10., pp. 839–841 (1998), which is incorporated herein by reference.

The signal monitor system for any of the above detection schemes can comprise any suitable digital signal processor capable of measuring the signal change from the detector 72 and transmitting that information to the user, such as, for example, a printed circuit board having a pre-amplifier, an AD converter and driver circuit, and a programmable chip for instrumentation specific software; or a multichip module comprising those elements.

A particular embodiment of the electrophoretic molecular sieve 40, shown in FIG. 5 and described above the self-assembled nano-array sieve 54 is fabricated according to the design shown in FIGS. 1 and 4 via the process outlined in FIGS. 3a to 3d, comprising a uniform array 54 of uniform self-assembled carbon nanotube nano-features having a mean diameter of ~15 nm and a pore size of about ~30 nm on a 10 mm substrate. A combination DC and pulsed electric field generator 56 is utilized to supply the electric field 64 to the sieve 54.

A comparison of the design parameters of the electrophoretic molecular sieve device 40 and the prior art electrophoretic devices is shown in Table 2, below.

TABLE 2

Device Design Parameters of Prior Art Devices and Prototype Device

| Device | Volkmuth | Duke | Turner | Proposed | Prototype |
|---|---|---|---|---|---|
| Technique | E-beam Lithography | E-beam Lithography | E-beam Lithography | Nanotube Arrays | Nanotube Arrays |
| Post diameter | 1 mm | 1–2 mm | 100 nm | 10–100 nm | ~15 nm |
| Post Spacing | 2 mm | 2–4 mm | 200 nm | 30–100 nm | ~30 nm |
| PoreSize | 1 mm | 1–2 mm | 100 nm | 10–100 nm | ~15 nm |
| Device Size | | | 15 mm | <10 mm | <10 mm |
| Field Strength | 1 V/cm | ~3 V/cm | 1.3–13 V/cm | 10–1,000 V/cm | 10–1,000 V/cm |
| Field Type | DC | DC, Pulsed | DC | DC, Pulsed | DC, Pulsed |
| DNA | dsDNA | dsDNA | dsDNA | ssDNA, dsDNA | ssDNA |
| Process | Fractionation | Fractionation | Fractionation | Sequencing Fractionation | Sequencing |
| DNA Size Dynamics | 3–100 kbp Hooking | 10–200 kbp Hooking Linear Migration | 7.2–43 kbp | ~1 bp–Mbp | <1 kb |

The device 40 can be optimized for mutation detection using multiple DNA fragments generated by dideoxy fingerprinting reactions through a nano-DOVAM-S (Detection Of Virtually All Mutations-SSCP) data analysis technique. This type of technique utilizes conventional single-strand conformation polymorphism (SSCP), but is much more efficient at mutation detection because it provides the redundancy of electrophoresis under five sets of sensitive and complementary conditions. By varying the operating conditions of the instrument the effects of electrophoresis with different array matrices, buffers, temperatures, and additives on mutation detection can be determined. DOVAM-S is a robust method for scanning genomic DNA, its advantages include the parallel analysis of 45 to 50 samples using multiple amplified products per lane on each gel and the increase in sensitivity of mutation detection to~100%. Utilizing the nano-DOVAM-S method, mutations can be detected even if only one of the ten single-stranded segments displays an altered electrophoretic migration. A full discussion of the DOVAM-S technique is disclosed in, *BioTechniques*, vol. 26, pp. 932–942 (1999), which is incorporated herein by reference.

While the generic nature of the conditions for DOVAM-S and the marked effect of buffers, additives and temperature make it suitable for nano-array molecular sieve devices, alternative methods could be utilized, including simple SSCP, as well as SSCP in combination with another method in order to generate redundancy of mutation-containing segments, such as, for example, dideoxy fingerprinting (ddF) and bidirectional dideoxy fingerprinting (Bi-ddF) in which SSCP is combined with a Sanger dideoxy termination reaction using only one dideoxy terminator. Another alternative method is restriction endonuclease fingerprinting (REF) which combines SSCP with restriction endonuclease digestion to generate multiple mutation containing segments.

In the DOVAM-S process, the genomic DNA is first amplified by PCR to produce segments to be analyzed by nano-DOVAM-S. The use of an electrophoresis sieve device in the method nano-DOVAM-S should permit the use of extremely small volume preparations facilitating rapid PCR performance at much reduced cost. Several micro and nano-scale PCR methods are available including capillary microfabricated silicon microreactors coupled to micro-separation platforms for the preparation, performance and delivery of PCR, such as, for example, *J. Chromatogr. A.*, vol. 853, pp. 107–120 (1999). Micro/nano-PCR methodologies are currently commercially available or in development by Caliper and Nanogen. PCR primers are labeled with one of four fluorescent dyes used in the BigDye™ terminators manufactured by PE Applied Biosystems for ABI sequencing (R6G (green), ROX (red), R110 (blue), and TAMRA (black)). Several (up to 18) PCR products from one sample are typically pooled for the nano-DOVAM-S assay.

The samples would then be loaded into the apparatus and the device run such that the region of interest (150–300 nucleotides) migrated past the detector in approximately a 20 minute interval. Potentially a CCD detector could be utilized that would make 15 measurements per second over multiple array channels such that 18,000 measurements could be taken and analyzed in a single data run. Using 10 lanes and three samples with 20 segments each per lane, and detecting all lanes in parallel, the present technique could potentially scan 600 DNA segments per 20 minutes or 1–2 Mb of DNA per day, this is compared to the 1–2 Mb of DNA per month rate of analysis of conventional gel-electrophoresis techniques.

Utilizing the above technique, it is anticipated that mutations of various types, including missense, nonsense, splice mutations, insertions and deletions can be detected. Included among the point mutations are transitions (G:C>A:T at and not at CpG sites; A:T>G:C) and transversions (G:C>T:A; C>C:G; A:T>T:A; A:T>C:G). Although the above discussion has focused on utilizing the molecular sieve of the current invention for detecting mutations, such a device could be utilized for any purpose for which conventional gel-based and micro-machined molecular sieves can be used, such as, for example, DNA fingerprinting, sequencing, etc.

Although specific embodiments are disclosed herein, it is expected that persons skilled in the art can and will design alternative molecular sieves, methods to produce the molecular sieves and/or molecular sieve instruments that are within the scope of the following claims either literally or under the Doctrine of Equivalents.

What is claimed is:

1. An electrophoretic device for producing a mobility distribution in a sample containing a plurality of molecules comprising:
    a non-gel self-assembled nanofeature array sieve having proximal and distal ends, the sieve comprising a substrate made of a first material and a plurality of self-assembled nanofeatures made of a second material wherein each nanofeature has a center point, a cross-sectional dimension and an outer surface and wherein the nanofeatures are fixedly attached to the substrate in a an ordered periodic array such that the distance between the center points of two adjacent nanofeatures defines a regular lattice spacing and the distance between the outer surfaces of two adjacent nanofeatures defines a pore size for the sieve and wherein the pore size of the sieve is chosen such that a molecule of the sample can be transported through the sieve at a characteristic velocity, the ordered periodic array of nanofeatures being defined by a plurality of catalytic germination spots deposited in a corresponding ordered periodic array on the substrate, each of the nanofeatures being anchored to and self-assembled from a separate one of the plurality of catalytic germination spots;
    a molecular reservoir in fluid communication with the proximal end of the sieve for introducing the molecules into the sieve;
    a detector arranged at the distal end of the sieve such that the molecules passing out of the sieve are detected and a signal generated;
    an electrical field generator for producing an electric field in field communication with the sieve, the reservoir and the detector such that the electrical field induces the molecules in the reservoir to move through the sieve to the detector; and
    a monitor in signal communication with the detector to communicate the signal to a user.

2. The electrophoretic device according to claim 1, further comprising a sieve body having proximal and distal ends and defining an internal volume and wherein the sieve is confined within the internal volume.

3. The electrophoretic device according to claim 1, one of the substrate or sieve body is transparent.

4. The electrophoretic device according to claim 1 wherein the sieve body is made of a material selected from the group consisting of silicon, alumina, glass and plastic.

5. The electrophoretic device according to claim 1 wherein the substrate is made of a material selected from the group consisting of silicon, alumina, glass and plastic.

6. The electrophoretic device according to claim 5 wherein the substrate is further coated with a metal selected from the group consisting of gold, aluminum and titanium.

7. The electrophoretic device according to claim 5 wherein the metal is anodized Al.

8. The electrophoretic device according to claim 1 wherein the catalytic germination spots are made from a material selected from the group consisting of Ni, Co or a Ni/Co alloy.

9. The electrophoretic device according to claim 1 wherein the nanofeatures have a uniform size.

10. The electrophoretic device according to claim 1 wherein at least two differently dimensioned nanofeatures are disposed on the substrate surface.

11. The electrophoretic device according to claim 1 wherein the nanofeatures have a cross-sectional dimension of about 10 to 100 nm.

12. The electrophoretic device according to claim 1 wherein the array has a lattice spacing of about 10 to 100 nm.

13. The electrophoretic device according to claim 1 wherein the array has a pore size of about 10 to 100 nm.

14. The electrophoretic device according to claim 1 wherein the substrate has an area of about 1 $mm^2$ to 1 $cm^2$.

15. The electrophoretic device according to claim 1 wherein the periodic array is a uniform periodic array having a uniform lattice spacing between nanofeatures.

16. The electrophoretic device according to claim 1 wherein the periodic array has at least two different lattice spacings.

17. The electrophoretic device according to claim 1 wherein the periodic array is a staggered periodic array.

18. The electrophoretic device according to claim 1 wherein the nanofeatures are made of carbon.

19. The electrophoretic device according to claim 1 wherein the sieve body forms at least one channel.

20. The electrophoretic device according to claim 1 wherein the sieve body forms a plurality of parallel channels.

21. The electrophoretic device according to claim 1 wherein the detector is a laser induced fluorescence spectrometer.

22. The electrophoretic device according to claim 1 wherein the detector comprises a binary supergrating optic.

23. The electrophoretic device according to claim 22 wherein the detector comprises a photodiode array comprising a plurality of spatially separated photodiodes.

24. The electrophoretic device according to claim 1 wherein the detector comprises a CCD camera.

25. The electrophoretic device according to claim 1 wherein the electrical field generator is a pair of electrodes.

26. The electrophoretic device according to claim 1 wherein the electric field is a constant DC field having a DC field vector and a field strength.

27. The electrophoretic device according to claim 26 wherein the electric field further comprises a pulsed field having a pulsed field vector angled transverse to the DC field vector.

28. The electrophoretic device according to claim 26 wherein the field strength is about 10 to 10,000 V/cm.

29. The electrophoretic device according to claim 1 wherein the molecules have a size of about 3 bp to 100 Mbp.

30. The electrophoretic device according to claim 1 wherein the molecules are DNA or RNA.

31. The electrophoretic device according to claim 1 wherein the molecules are labeled with a dye.

32. The electrophoretic device according to claim 1 wherein the reservoir comprises one device selected from the group consisting of an agarose gel, an electrokinetic injector and a positively charged gold wire.

33. The electrophoretic device according to claim 1 wherein the nanofeatures are chemically functionalized.

34. The array sieve according to claim 1 wherein the nanofeatures are grown by self-assembly on the substrate.

35. The array sieve according to claim 1 wherein the nanofeatures are nanotubes.

36. The array sieve according to claim 1 wherein the characteristic velocity of the molecules is size dependent.

37. A method of separating molecules in a sample by size dependent mobility comprising utilizing an electrophoretic device according to claim 1.

38. A method of separating a plurality of molecules in a sample comprising the steps of:

providing a non-gel self-assembled nanofeature array sieve having proximal and distal ends, the sieve comprising a substrate made of a first material and a plurality of self-assembled nanofeatures made of a second material wherein each nanofeature has a center point, a cross-sectional dimension and an outer surface and wherein the nanofeatures are fixedly attached to the substrate in an ordered periodic array such that the distance between the center points of two adjacent nanofeatures defines a regular lattice spacing and the distance between the outer surfaces of two adjacent nanofeatures defines a pore size for the sieve and wherein the pore size of the sieve is chosen such that a molecule of the sample can be transported through the sieve at a characteristic velocity, the ordered periodic array of nanofeatures being defined by a plurality of catalytic germination spots deposited in a corresponding ordered periodic array on the substrate, each of the nanofeatures being anchored to and self-assembled from a separate one of the plurality of catalytic germination spots;

introducing the sample into the proximal end of the sieve;

applying power to an electrical field generator in field communication with the sieve such that an electric field having a field vector and a field strength is projected from the proximal to the distal end of the sieve such that the sample is induced to move from the proximal to the distal end of the sieve; and detecting the distribution of the sample at the distal end of the sieve and communicating the distribution to a user.

39. The method according to claim 38 wherein the characteristic velocity of the molecules is size dependent.

40. The method according to claim 38 wherein the nanofeatures are nanotubes.

* * * * *

UNITED STATES PATENT AND TRADEMARK OFFICE
CERTIFICATE OF CORRECTION

PATENT NO. : 6,685,810 B2
DATED : February 3, 2004
INVENTOR(S) : Noca et al.

It is certified that error appears in the above-identified patent and that said Letters Patent is hereby corrected as shown below:

Title page,
Item [56], References Cited, OTHER PUBLICATIONS, delete "Avrutsky, et al. ("Multiwavelength Diffraction and Apodization using Binary Superimposed Gratings," IEEE Photonics Technology Letters, vol. 10, No. 6, Jun 1998).*"
"Liu, Q. et al." reference, delete "Virtually 100
     Sensitity; BioTechniques",
     insert
     -- Virtually 100% Sensitivity; BioTechniques --
"Schmalzing, Dieter et al." reference, after "pp. 853-858", insert -- ; --
"Soper, Steven A." reference, delete "polymethylmetharcrylate-based", insert -- polymethylmethacrylate-based --
"Yoon, Dy et al." reference, delete "ploystyrene", insert -- polystyrene --
"Zhang, Yuegang et al." reference, delete "Electric-field directed", insert -- Electric-field-directed --
Item [57], ABSTRACT,
Line 1, delete "invention are" insert -- invention is --

Column 15,
Line 18, delete "a an ordered periodic", insert -- an ordered periodic --
Line 48, delete "according to claim 1, one", insert -- according to claim 1 wherein --

Column 16,
Line 46, delete "transverse", insert -- transversely --

Signed and Sealed this

Twenty-eighth Day of June, 2005

JON W. DUDAS
*Director of the United States Patent and Trademark Office*